(12) United States Patent
Duffield

(10) Patent No.: US 11,534,348 B2
(45) Date of Patent: Dec. 27, 2022

(54) LINED PAD HYBRID

(71) Applicant: Chrisette Duffield, Oak Hill, WV (US)

(72) Inventor: Chrisette Duffield, Oak Hill, WV (US)

( * ) Notice: Subject to any disclaimer, the term of this patent is extended or adjusted under 35 U.S.C. 154(b) by 306 days.

(21) Appl. No.: 16/873,666

(22) Filed: May 8, 2017

(65) Prior Publication Data

US 2021/0170064 A1 Jun. 10, 2021

(51) Int. Cl.
| | |
|---|---|
| *A61F 13/472* | (2006.01) |
| *A61L 15/22* | (2006.01) |
| *A61F 13/53* | (2006.01) |
| *A61F 13/15* | (2006.01) |

(52) U.S. Cl.
CPC ...... *A61F 13/47218* (2013.01); *A61L 15/225* (2013.01); *A61F 2013/15357* (2013.01); *A61F 2013/530036* (2013.01)

(58) Field of Classification Search
CPC ...... A61F 13/47218; A61F 2013/51035; A61F 2013/530036; A61F 2013/49084; A61F 2013/00578; A61F 2013/15357; A61L 15/225
See application file for complete search history.

(56) References Cited

U.S. PATENT DOCUMENTS

| | | | | |
|---|---|---|---|---|
| 4,490,147 A | * | 12/1984 | Pierce | A61F 13/47218 604/385.101 |
| 5,092,860 A | * | 3/1992 | Pigneul | A61F 13/47218 604/385.05 |
| 5,454,802 A | * | 10/1995 | Lindquist | A61F 13/47263 604/385.05 |
| 5,545,156 A | * | 8/1996 | DiPalma | A61F 13/51401 604/378 |
| 5,599,337 A | * | 2/1997 | Mccoy | A61F 13/4753 604/385.01 |
| 6,231,556 B1 | * | 5/2001 | Osborn, III | A61F 13/15203 604/358 |
| 6,475,199 B1 | * | 11/2002 | Gann | A61F 13/47227 604/385.01 |
| 6,613,955 B1 | * | 9/2003 | Lindsay | A61F 13/4704 604/378 |
| 6,740,069 B2 | * | 5/2004 | Drevik | A61F 13/47263 604/385.01 |
| 2001/0047159 A1 | * | 11/2001 | Mizutani | A61F 13/47263 604/385.23 |
| 2006/0264885 A1 | * | 11/2006 | Carstens | A61F 13/4752 604/396 |

FOREIGN PATENT DOCUMENTS

EP 389023 A * 9/1990 ........... A61F 13/476

* cited by examiner

*Primary Examiner* — Daniel J Colilla

(57) ABSTRACT

The sanitary napkin has a semisolid (flexible) structure affixed along the center base of it. The semisolid flexible structure is an elongated form of matter that goes along the base of the sanitary napkin. Surrounding the affixed center base semisolid structure is material that is not semisolid or solid, but soft and consistent with the rest of the sanitary napkin.

1 Claim, 3 Drawing Sheets

LINED PAD HYBRID

BACKGROUND OF THE INVENTION

The lined pad hybrid relates to a sanitary napkin or menstrual pad and its ability to facilitate even and targeted absorbency.

Previous sanitary napkins maintained a flat, fairly even surface which, due to gravity and movement, made it more difficult to hold its protective barrier. Current designs do not include a supportive structure to better adhere to the body and prevent leaks. The lined pad hybrid would provide more structure to the areas in which a direct absorption can occur.

SUMMARY OF THE INVENTION

The sanitary napkin includes one major change to the common design today. It has a supportive flexible central structure that better contours to the body and facilitates contact in areas in which this would normally be excluded. Direct contact then supports direct absorption. This inevitably leads to a decrease in leaks and a more secure fit.

BRIEF DESCRIPTION OF THE INVENTION

Figure 1:
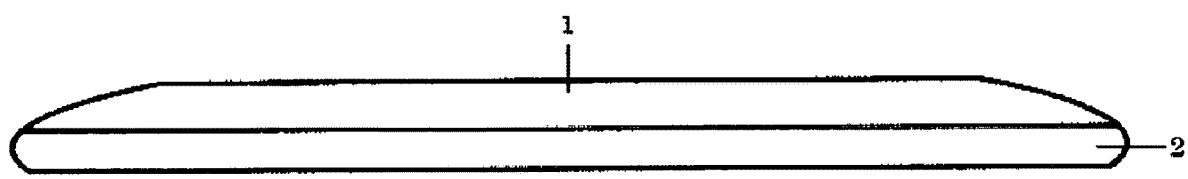
FIG. 1 is a depiction of the lined pad hybrid dissected in half from the side along the entire length of the pad.
Figure 2:
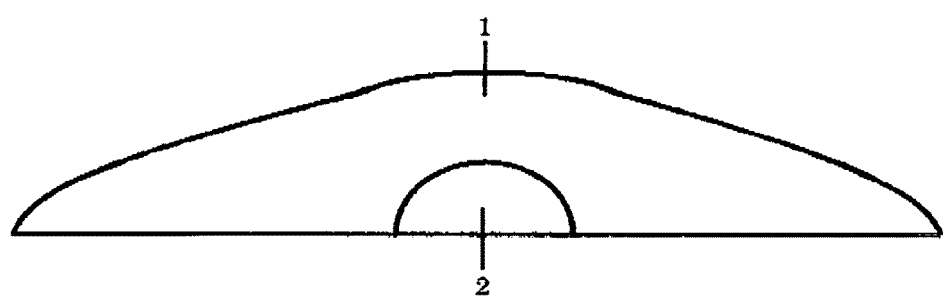
FIG. 2 depicts the lined hybrid pad dissected in half at mid length and displaying the full width of the pad.
Figure 3:
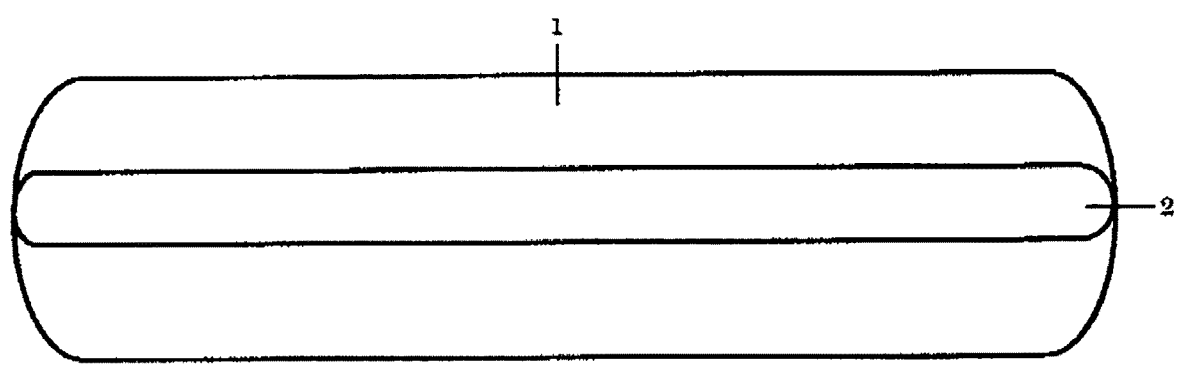

FIG. 3 displays the pad's full width and length dissected in half from the top, with the base structure of the pad visible.

Figure 4:

FIG. 4 is a view of the pad length with no dissection.

Figure 5:
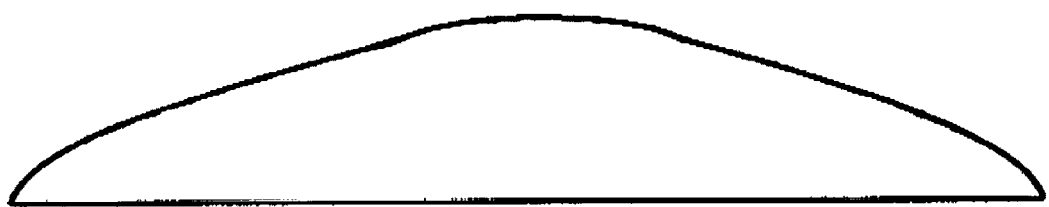

FIG. 5 is a view of the pad width with no dissection.

Figure 6:

FIG. 6 is a view of the pad from above with no dissection.

DETAILED DESCRIPTION OF THE INVENTION

The concept introduced in the lined pad hybrid is the semisolid (flexible) structure, 2, affixed to the base of the sanitary napkin and the benefits offered by adding structural integrity to a sanitary napkin. The semisolid structure, 2, is further secured to the base by an absorbent sheet layer material, 1.

The semisolid core, 2, addresses the issue of having a sanitary napkin which fits securely to the body. The absorbent layer, 1, surrounding the semisolid core, 2, provide both additional structural integrity of the semisolid core, 2, and comfort of the sanitary napkin itself. The absorbent layer, 2, provides a cushioning that even further facilitates a more secure fit as it assists the sanitary napkin to further adapt to the shape of the body. The semisolid core, 2, is designed to provide and maintain structural integrity where it is needed which better resolves the issue of leaks due to gravity and motion.

The invention claimed is:

1. A hybrid sanitary pad comprising:
   a semi-solid, semi-cylindrical structure disposed in a center of the pad and extending an entire length of the pad, said semi-solid, semi-cylindrical structure comprising a mixture of rayon and cotton; and
   a cotton layer disposed on left and right sides of the semi-solid, semi-cylindrical structure and passing over a top of the semi-solid, semi-cylindrical structure,
   wherein a flat surface of said semi-solid, semi-cylindrical structure is exposed to form a portion of a bottom surface of the pad, and
   wherein said semi-solid, semi-cylindrical structure forms a hump in a top surface of said pad, said hump extending an entire length of said pad.

* * * * *